United States Patent [19]

Plummer

[11] Patent Number: 4,636,523

[45] Date of Patent: Jan. 13, 1987

[54] INSECTICIDAL UREA SUBSTITUTED 2,3-DIHYDRO- BENZOFURAN AND BENZOTHIOPHENE DERIVATIVES, COMPOSITIONS, AND METHOD OF USE THEREOF

[75] Inventor: Ernest L. Plummer, Yardley, Pa.

[73] Assignee: FMC Corporation, Philadelphia, Pa.

[21] Appl. No.: 816,661

[22] Filed: Jan. 7, 1986

[51] Int. Cl.$^4$ .................... A01N 43/10; A01N 43/12; C07D 307/78; C07D 333/52

[52] U.S. Cl. .................... 514/443; 514/469; 549/57; 549/438; 549/439

[58] Field of Search .................... 549/57, 438, 439; 514/443, 447, 469, 470

[56] References Cited

U.S. PATENT DOCUMENTS

| | | | |
|---|---|---|---|
| 3,709,909 | 1/1973 | Habicht | 549/57 |
| 4,013,717 | 3/1977 | Wellinga et al. | 260/553 |
| 4,053,484 | 10/1977 | Asato | 549/57 |

OTHER PUBLICATIONS

K. Wellinga, R. Mulder, and J. J. van Daalen, J. Agr. Food Chem., 21 (3), 348, 1973.

K. Wellinga, R. Mulder, and J. J. van Daalen, J. Agr. Food Chem., 21 (6), 993, 1973.

Primary Examiner—Henry R. Jiles
Assistant Examiner—J. G. Mullins
Attorney, Agent, or Firm—William Schmonsees; H. Robinson Ertelt

[57] ABSTRACT

Insecticidal compounds of the formula

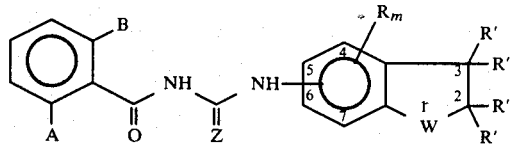

in which A and B are both halogen or hydrogen, or one of A and B is hydrogen, and the other of A and B is halogen; Z and W are independently O or S; the substituted benzofuranyl or benzothienyl group is attached at position 5 or 6; R is halogen; m is 0 to 3; R' is F or $CF_3$; methods for their preparation and formulation, insecticidal compositions, and their use to control insects are disclosed.

11 Claims, No Drawings

INSECTICIDAL UREA SUBSTITUTED 2,3-DIHYDRO- BENZOFURAN AND BENZOTHIOPHENE DERIVATIVES, COMPOSITIONS, AND METHOD OF USE THEREOF

RELATED APPLICATION

This application is related to commonly assigned application Ser. No. 725,193, filed Apr. 19, 1985, of D. E. Seelye and E. L. Plummer entitled "Tetrafluoro Benzofurans and Process of Preparation".

BACKGROUND OF THE INVENTION

This invention relates to new insect growth regulators, or development disrupters, which effectively control infestations of undesirable insects by interfering with the normal molting process of insect larvae. The utility of benzoylureas as insect growth regulators was noted in the pioneering work of Wellinga, U.S. Pat. No. 4,013,717, culminating in the commercialization of diflubenzuron. Numerous compounds, all closely related to diflubenzuron, have since been reported as insect development disrupters.

The present invention discloses second generation benzoylureas, incorporating novel fluorinated benzofurans and benzothiophenes, which are significantly more potent than those known in the art.

SUMMARY OF THE INVENTION

The compounds of this invention have the general formula (I):

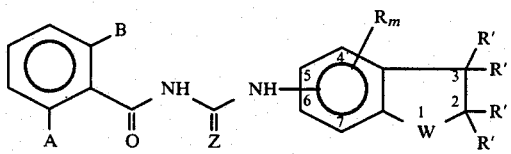

in which A and B are both halogen, or one of A and B is hydrogen and the other of A and B is halogen, W and Z may be either oxygen or sulfur, the benzofuranyl or benzothienyl group is attached at position 5 or 6, $R_m$ is any art-recognized substituent commonly used on phenyl groups, m is 0 to 3, and R' is F or $CF_3$, with the proviso that only one of R' may be $CF_3$.

This invention also encompasses insecticidal compositions containing the benzoylureas and their use for controlling insects.

DETAILED DESCRIPTION

In the compounds of formula I, A and B are both fluorine, chlorine, bromine or iodine, or one of A and B is fluorine, chlorine, bromine, or iodine, and the other of A and B is hydrogen. Preferably A and B are both fluorine.

W and Z may be either oxygen or sulfur, independently of each other. Preferably both W and Z are oxygen.

$R_m$ is selected from halogen, hydroxyl, alkyl, alkoxy, haloalkyl, haloalkoxy, acyl, acyloxy, aryl, aryloxy, alkoxycarbonyl, alkoxycarbonylalkyl, alkylamino, alkylthio, nitro, or cyano. The terms "alkyl" and "alkoxy" mean a straight or branched hydrocarbon chain of 1–6, preferably 1–4, carbon atoms. "Aryl" includes both substituted and unsubstituted phenyl groups.

R' is fluorine or trifluoromethyl, and may include other halogenated lower alkyl groups.

The compounds of this invention are prepared as follows:

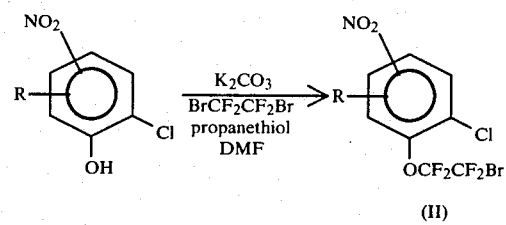

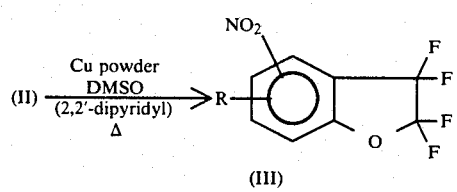

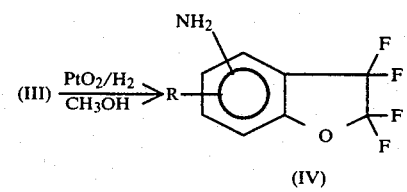

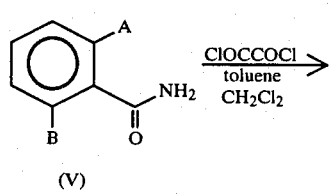

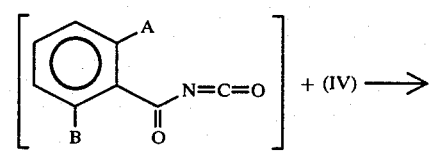

A substituted 2-chloro-4-or-5-nitrophenol is heated in a pressure bottle with potassium carbonate, 1,2-dibromotetrafluoroethane, a catalytic amount of propanethiol and N,N-dimethylformamide to produce the substituted chloro-(2-bromo-1,1,2,2-tetrafluoroethoxy)nitrobenzene (II). Heating compound (II) in a pressure bottle with copper powder, with or without a catalytic amount of 2,2'-bipyridyl, in dimethyl sulfoxide (DMSO), produces the substituted 2,2,3,3-tetrafluoronitrobenzofuran (III). Hydrogenation of compound (III) with a catalytic amount of platinum oxide in methanol yields the corresponding amine (IV).

A substituted benzamide (V) is heated with oxalyl chloride in a solution of toluene and methylene chloride for several hours to produce the corresponding isocyanate intermediate. The amine (IV) is added to the isocyanate intermediate, still in solution, to produce the 2,2,3,3-tetrafluorobenzofuranyl benzoylurea (I).

Further details, and alternative synthetic routes to the amine (IV), are disclosed in copending application, U.S. Ser. No. 725,193, filed Apr. 19, 1985.

Benzoylureas of formula I exhibit good insecticidal activity against southern armyworm (*Spodoptera eridania*), Mexican bean beetle (*Epilachna varivestis*), and cabbage looper (*Trichoplusia ni*). For example, a benzoylurea of formula I wherein A and B are fluorine, R is 7-chloro, R' is fluoro, W and Z are oxygen, and the benzoylurea is attached at position 5 exhibited 100% mortality against the southern armyworm at a concentration of 2 ppm. Against the cabbage looper, 100% mortality at 2 ppm concentration was achieved by application of the same benzoylurea.

The benzoylureas of formula I are employed as insecticides in the conventional manner. Accordingly, they may be applied neat, but more usually are formulated as blends with agriculturally acceptable carriers and surfactants and applied as sprays, dusts, or granules to the locus where pest control is desired. Type of formulation and concentration of benzoylurea will vary according to the pest and the environment. Thus, the benzoylureas may be formulated as granules of large particle size, as powdery dusts, as wettable powders, as emulsifiable concentrates, as solutions, or in other form. When a formulation is diluted for application, the benzoylurea will normally be present in the range of about 0.001% to about 10% by weight. The locus of application may be the insects themselves, plants upon which the insects feed, or the insect habitat, including soil in which plants are, or are about to be, planted.

The following examples will serve as further illustration of the invention but are not intended necessarily as limitations on the scope thereof. In the examples and elsewhere in this specification, all parts and percentages are by weight, all temperatures are °C., and all pressures are mm Hg, unless otherwise stated.

EXAMPLE 1

N-[[(2,2,3,3,-Tetrafluoro-2,3-dihydrobenzofuran-5-yl)amino]-carbonyl]-2,6-difluorobenzamide

Step A
3-Chloro-4-(2-bromo-1,1,2,2-tetrafluoroethoxy)nitrobenzene

Into a pressure bottle were placed 5.0 g (0.029 mole) 2-chloro-4-nitrophenol, 5.0 g (0.036 mole) potassium carbonate, 1.0 g (0.013 mole) propanethiol, 11.2 g (0.043 mole) 1,2-dibromotetrafluoroethane and 100 ml of N,N-dimethylformamide. The pressure bottle was sealed and the mixture stirred at 50° C. for 48 hours. The pressure bottle was cooled to room temperature, opened, and the contents poured into a separatory funnel. Approximately 200 ml of a 2N sodium hydroxide solution was added to the separatory funnel. The resultant mixture was extracted with four 300 ml portions of diethyl ether. The extracts were combined and washed with two 100 ml portions of a 2N sodium hydroxide solution. The washed extract was dried over anhydrous magnesium sulfate and filtered. The filtrate was evaporated under reduced pressure leaving an oil. The reaction described above was repeated four additional times. The residual oils from the five experiments were combined and purified by column chromatography on silica gel, eluting with n-heptane:toluene (95:5), to yield 3-chloro-4-(2-bromo-1,1,2,2-tetrafluoroethoxy)nitrobenzene as an oil.

Analysis calc'd for $C_8H_3BrClF_4NO_3$: C, 27.26; H, 0.86; Found: C, 27.54; H, 0.97.

Step B
2,2,3,3-Tetrafluoro-2,3-dihydro-5-nitrobenzofuran

Into a pressure bottle were placed 3.0 g (0.0085 mole) 3-chloro-4-(2-bromo-1,1,2,2-tetrafluoroethoxy)nitrobenzene, 2.7 g (0.043 mole) copper powder (200 mesh), and 40 ml of dimethyl sulfoxide. The pressure bottle was sealed, and the reaction mixture stirred at 190°-195° C. for 6.5 hours. The pressure bottle was cooled to room temperature, opened, and the contents poured into a separatory funnel. Approximately 200 ml of water was added to the separatory funnel, and the mixture was extracted with three 150 ml portions of diethyl ether. The extracts were combined and washed first with 200 ml of a 2N hydrochloric acid solution, then with 200 ml of a saturated aqueous sodium chloride solution. The washed extract was dried over anhydrous magnesium sulfate and filtered. The solvent was evaporated under reduced pressure, leaving an oil. The reaction described above was repeated one additional time. The residual oils from the two experiments were combined and upon standing formed crystals of 2,2,3,3-tetrafluoro-2,3-dihydro-5-nitrobenzofuran.

Step C
5-Amino-2,2,3,3-tetrafluoro-2,3-dihydrobenzofuran

Hydrogenation of 2.1 g (0.009 mole) 2,2,3,3-tetrafluoro-2,3-dihydro-5-nitrobenzofuran with a catalytic amount (0.2 g) of platinum oxide in 150 ml of methanol produced 0.79 g of 5-amino-2,2,3,3-tetrafluoro-2,3dihydrobenzofuran. The nmr spectra was consistent with the proposed structure.

Step D
N-[[(2,2,3,3-Tetrafluoro-2,3-dihydrobenzofuran-5-yl)-amino]carbonyl]-2,6-difluorobenzamide Under a dry nitrogen atmosphere a mixture of 0.55 g (0.0035 mole) 2,6-difluorobenzamide, 0.48 g (0.0038 mole) oxalyl chloride, and 70 ml of toluene was heated at reflux for two hours. The mixture was cooled and distilled under reduced pressure to remove excess oxalyl chloride and approximately 60 ml of toluene. To the pot residue were added 30 ml of fresh toluene and 0.72 g (0.0035 mole) 5-amino-2,2,3,3-tetrafluoro-2,3-dihydrobenzofuran dissolved in 30 ml of toluene. The resultant mixture was allowed to stir at room temperature for approximately 18 hours. Approximately 100 ml of n-pentane was added to this mixture. A white precipitate formed after stirring for an additional hour. This solid was collected by filtration to yield 0.74 g of N-[[(2,2,3,3-tetrafluoro-2,3-dihydrobenzofuran-5-yl)amino]carbonyl]-2,6-difluorobenzamide (mp 183°-184.5° C.), Compound 1 of Table 1. The nmr and ir spectra were consistent with the proposed structure.

EXAMPLE 2

N-[[(7-Chloro-2,2,3,3-Tetrafluoro-2,3-dihydrobenzofuran-5-yl)-amino]carbonyl]-2-chlorobenzamide

Step A
4-(2-Bromo-1,1,2,2-tetrafluoroethoxy)-3,5-dichloroaniline

In a manner similar to Step A of Example 1, the reaction of 12.5 g 0.07 mole) 4-amino-2,6-dichlorophenol, 7.3 g (0.053 mole) potassium carbonate, 1.0 g (0.013 mole) propanethiol, 36.5 g (0.14 mole) 1,2-dibromotetrafluoroethane and 125 ml of N,N-dimethylformamide produced 3.7 g of 4-(2-bromo-1,1,2,2-tetrafluoroethoxy)-3,5-dichloroaniline as an oil.

The above reaction was repeated one additional time to yield 3.1 g of product.

Step B
N-[4-(2-Bromo-1,1,2,2-tetrafluoroethoxy)-3,5-dichlorophenyl]phthalimide A mixture of 6.8 g (0.019 mole) 4-(2-bromo-1,1,2,2-tetrafluoroethoxy)-3,5-dichloroaniline, 2.8 g (0.019 mole) phthalic anhydride and 75 ml of glacial acetic acid was heated at reflux for approximately 18 hours. Most of the acetic acid was removed by distillation under reduced pressure, leaving a residue. This residue was extracted with three 150 ml portions of diethyl ether. The extracts were combined and washed with two 200 ml portions of a 2N sodium hydroxide solution. The washed extract was dried over anhydrous magnesium sulfate and filtered. The filtrate was evaporated under reduced pressure to leave an oil which solidified upon standing. This solid was subjected to column chromatography on silica gel, eluting with toluene, yielding 6.4 g of an oil which again solidified upon standing. Purification of this solid by recrystallization from methylcyclohexane provided 5.4 g of N-[4-(2-bromo-1,1,2,2-tetrafluoroethoxy)-3,5-dichlorophenyl]phthalimide (mp 62°–63.5° C.). The nmr and ir spectra were consistent with the proposed structure.

Analysis calc'd for $C_{16}H_6BrCl_2F_4NO_3$: C, 39.46; H, 1.24; Found: C ,39.84; H, 1.03.

Step C
N-[7-Chloro-2,2,3,3-tetrafluoro-2,3-dihydrobenzofuran-5-yl]phthalimide A mixture of 4.4 g (0.0090 mole) 1-[4-(2-bromo-1,1,2,2-tetrafluoroethoxy)-3,5-dichlorophenyl]-phthalimide, 2.9 g (0.045 mole) copper powder (200 mesh, activated by treating copper powder in acetone with anhydrous iodine as described in Organic Synthesis, III, p. 339), and 0.70 g (0.0045 mole) 2,2'-dipyridyl in 70 ml of dimethyl sulfoxide was heated to 148° C. After 30 minutes the reaction mixture was cooled to about 20° C. using an ice bath. The cooled reaction mixture was poured into 200 ml of a 2N hydrochloric acid solution. The resultant mixture was stirred for a brief period while being cooled in an ice bath, then was extracted with three 200 ml portions of diethyl ether. The organic extracts were combined, filtered, and washed in succession with 100 ml 2N hydrochloric acid, three 100 ml portions of a 2N sodium hydroxide solution, and two 100 ml portions of aqueous saturated sodium chloride solution. The washed organic phase was dried over anhydrous magnesium sulfate and filtered. The filtrate was evaporated under reduced pressure, leaving a solid. This solid was purified by recrystallization from methylcyclohexane to yield 2.7 g of N-[4-(2-bromo-1,1,2,2-tetrafluoroethoxy)-3,5-dichlorophenyl]phthalimide (mp 135.5°–137° C.). The nmr and ir spectra were consistent with the proposed structure.

Analysis calc'd for $C_{16}H_{16}ClF_4NO_3$: C, 51.71; H, 1.63; Found: C, 52.30; H, 1.70.

Step D
5-Amino-7-chloro-2,2,3,3-tetrafluoro-2,3-dihydrobenzofuran

A mixture of 2.3 g N-[4-(2-bromo-1,1,2,2-tetrafluoroethoxy)-3,5-dichlorophenyl]phthalimide (0.0062 mole) and 0.25 g (0.0068 mole) hydrazine hydrate in 50 ml of ethanol was heated at reflux for one hour. Most of the solvent was removed by distillation under reduced pressure, and the residual liquid was poured into water. This mixture was extracted with three 150 ml portions of diethyl ether and the extracts were combined. This organic solution was washed with 200 ml of an aqueous 2N sodium hyroxide solution. The washed organic solution was dried over anhydrous magnesium sulfate and filtered. The filtrate was evaporated under reduced pressure to yield 5-amino-7-chloro-2,2,3,3-tetrafluoro-2,3-dihydrobenzofuran as an oil. The nmr and ir spectra were consistent with the proposed structure.

Step E
N-[[(7-Chloro-2,2,3,3-tetrafluoro-2,3-dihydrobenzofuran-5-yl)amino]carbonyl]-2-chlorobenzamide In a manner similar to Step D of Example 1 the reaction of 0.58 g (0.0037 mole) 2-chlorobenzamide and 0.52 g (0.0041 mole) oxalyl chloride in 70 ml of toluene and 5 ml of methylene chloride followed by 0.90 g (0.0037 mole) 5-amino-7-chloro-2,2,3,3-tetrafluoro-2,3-dihydrobenzofuran produced an oil. This oil was subjected to column chromatography on silica gel, eluting with toluene, to provide a solid. Recrystallization of this solid from methylcyclohexane:toluene (90:10) yielded 0.76 g of N-[[(7-chloro-1,1,3,3-tetrafluoro-2,3-dihydrobenzofuran-5-yl)amino]carbonyl]-2-chlorobenzamide (mp 142°–143° C.), Compound 5 of Table 1. The nmr and ir spectra were consistent with the proposed structure.

EXAMPLE 3

N-[[(7-chloro-2,2,3,3-tetrafluoro-2,3-dihydrobenzothien-5-yl)-amino]carbonyl]-2-chlorobenzamide

Step A
2-(2-Bromo-1,1,2,2-tetrafluoroethylthio)-1,3-dichlorobenzene

In a manner similar to Step A of Example 1, the reaction of 26.0 g (0.25 mole) 2,6-dichlorothiophenol, 20.0 g (0.15 mole) potassium carbonate and 75.4 g (0.30 mole) 1,2-dibromotetrafluoroethane in 200 ml of N,N-dimethylformamide produced 31.5 g of 2-(2-bromo-1,1,2,2-tetrafluoroethylthio)-1,3-dichlorobenzene as an oil. The nmr and ir spectra were consistent with the proposed structure.

Step B
4-(2-Bromo-1,1,2,2-tetrafluoroethylthio)-3,5-dichloronitrobenzene

A stirred mixture of 30.5 g (0.085 mole) 2-(2-bromo-1,1,2,2-tetrafluoroethylthio)-1,3-dichlorobenzene and 13.3 g (0.10 mole) nitronium tetrafluoroborate (0.5M in sulfone) was heated at 100° C. for approximately 18 hours. An additional 4.0 g of nitronium tetrafluoroborate (solid) was added to the reaction mixture and heating was continued for 14 hours. The mixture was cooled and poured into 200 g of ice water. The resultant mixture was extracted with four 100 ml portions of methylene chloride and the extracts were combined. The organic extract was extracted with three 100 ml portions of a 2N sodium hydroxide solution. The basic aqueous extracts were combined and washed with 100 ml of methylene chloride. The washed extract was made acidic with concentrated hydrochloric acid while cooling in an ice bath. The acidic solution was saturated with sodium chloride and then was extracted with three 150 ml portions of methylene chloride. The organic extracts were combined and dried over anhydrous magnesium sulfate. After filtering the filtrate was evaporated under reduced pressure to leave an oil. This oil was subjected to column chromatography on silica gel, elution with n-heptane, to leave an oil after combining and evaporating the appropriate fractions. This oil was dissolved in n-heptane, leaving a small amount of solid which was removed by filtration. The filtrate was reduced in volume by evaporation under reduced pressure. An oil separated from the n-heptane solution and was removed by pipette. This oil (20.4 g) was found to be unreacted 1-(2-bromo-1,1,2,2-tetrafluoroethylthio)-2,6-dichlorobenzene. The remaining n-heptane was evaporated under reduced pressure to leave 13.3 g of 4-(2-bromo-1,1,2,2-tetrafluoroethylthio)-3,5-dichloronitrobenzene as an oil.

Analysis calc'd for $C_8H_2BrCl_2F_4NO_2S$: C, 23.84; H, 0.50; Found: C, 24.59; H, 0.70.

The nmr and ir spectra were consistent with the proposed structure.

The recovered 1-(2-bromo-1,1,2,2-tetrafluoroethylthio)-2,6-dichlorobenzene (20.4 g) was added to a reaction flask containing 10 ml concentrated sulfuric acid and 20 ml concentrated nitric acid. After complete addition the mixture was heated at 90° C. and stirred for two hours. An additional 20 ml nitric acid was added and the reaction mixture was stirred at 90° C. for approximately 18 hours. The mixture was cooled and poured into 300 ml of ice water. The aqueous mixture was extracted with three 150 ml portions of methylene chloride and the extracts were combined. The extract was washed with three 150 ml portions of a 2N sodium hydroxide solution. The organic phase was dried over anhydrous magnesium sulfate and filtered. The filtrate was evaporated under reduced pressure to leave an oil. This oil was purified by column chromatography on silica gel, elution with n-heptane:toluene (90:10), to yield 14.6 g of 4-(2-bromo-1,1,2,2-tetrafluoroethylthio)-3,5-dichloronitrobenzene as an oil. This sample was combined with the previously prepared sample to provide a total of 27.9 g.

Step C

7-Chloro-2,2,3,3-tetrafluoro-2,3-dihydro-5-nitrobenzothiophene

Under a dry argon atmosphere a stirred mixture of 18.8 g (0.047 mole) 4-(2-bromo-1,1,2,2-tetrafluoroethylthio)-3,5-dichloronitrobenzene, 14.8 g (0.23 mole) cooper powder, and 7.3 g (0.0478 mole) 2,2'-dipyridyl in 300 ml of dimethyl sulfoxide was heated at 150° C. for 15 minutes. The mixture was cooled and poured into a separatory funnel containing approximately 100 g of 2N hydrochloric acid. The aqueous mixture was extracted with three 150 ml portions of diethyl ether and the extracts were combined. The extract was washed in succession with two 100 ml portions of 2N hydrochloric acid, two 100 ml portions of a saturated aqueous sodium chloride solution, two 100 ml portions of 2N sodium hydroxide, and 100 ml of 2N hydrochloric acid. The washed organic solution was dried over anhydrous magnesium sulfate and filtered. The filtrate was evaporated under reduced pressure to leave an oil. This oil was subjected to column chromatography on silica gel, elution with n-heptane:toluene (90:10), to provide a solid after evaporation of the appropriate fractions. This solid was recrystallized from n-heptane to yield 7.5 g 7-chloro-2,2,3,3-tetrafluoro-2,3-dihydro-5-nitrobenzothiophene (mp 61.5°–62° C.).

The nmr and ir were consistent with the proposed structure.

Analysis calc'd for $C_8H_2ClF_4NO_2S$: C, 33.41; H, 0.70: Found: C, 34.06; H, 0.71.

Step D

5-Amino-7-chloro-2,2,3,3-tetrafluoro-2,3-dihydrobenzothiophene

Hydrogenation of 2.1 g (0.0073 mole) 7-chloro-2,2,3,3-tetrafluoro-2,3-dihydro-5-nitrobenzothiophene with a catalytic amount (0.25 g) of platinum oxide in 100 ml of methanol produced 1.9 g of 5-amino-7-chloro-2,2,3,3-tetrafluoro-2,3-dihydrobenzothiophene.

The ir spectrum was consistent with the proposed structure.

Step E

N-[[(7-Chloro-2,2,3,3-tetrafluorobenzothien-5-yl)amino]carbonyl]-2-chlorobenzamide In a manner similar to Step D of Example 1, the reaction of 0.58 g (0.0037 mole) 2-chlorobenzamide, 0.52 g (0.0051 mole) oxalyl chloride, 0.95 g (0.0037 mole) 5-amino-7-chloro-2,2,3,3-tetrafluoro-2,3-dihydrobenzothiophene, and 5 ml of methylene chloride in 75 ml of toluene produced 0.84 g of N-[[(7-chloro-2,2,3,3-tetrafluorobenzothien-5-yl)amino]-carbonyl]-2-chlorobenzamide as a solid (mp 140°–142° C.), compound 9 of Table 1.

The nmr and ir spectra were consistent with the proposed structure.

Analysis calc'd for $C_{16}H_8Cl_2F_4N_2O_2S$: C, 43.75; H, 1.83; Found: C, 45.41; H, 1.77.

EXAMPLE 4

N-[[(7-chloro-2,2,3-trifluoro-3-trifluoromethyl-2,3-dihydrobenzofuran-5-yl)amino]carbonyl]-2,6-difluorobenzamide

Step A 2-(2-Bromo-1,1,2,3,3,3-hexafluoropropanoxy)-1,3-dichlorobenzene

In a manner similar to Step A of Example 1, the reaction of 16.3 g (0.10 mole) 2,6-dichlorophenol, 13.8 g (0.10 mole) potassium carbonate, 1.0 g (0.013 mole) propanethiol, 62.0 g (0.20 mole) 1,2-dibromohexafluoropropane, and 125 ml of N,N-dimethylformamide produced 33.0 g of 2-(2-bromo-1,1,2,3,3,3-hexafluoropropanoxy)-1,3-dichlorobenzene as an oil. The ir spectra was consistent with the proposed structure.

Analysis calc'd for $C_9H_3BrCl_2F_6O$: C, 27.58; H, 0.77; Found: C, 27.44; H, 0.74.

Step B
7-Chloro-2,2,3-trifluoro-3-trifluoromethyl-2,3-dihydrobenzofuran

In a manner similar to Step C of Example 2, the reaction of 12.8 g (0.033 mole) 2-(2-bromo-1,1,2,3,3,3-hexafluoropropanoxy)-1,3-dichlorobenzene, 10.4 g (0.16 mole) activated copper powder, and 2.3 g (0.0033 mole) bis(triphenylphosphine)palladium II chloride in 225 ml of dimethyl sulfoxide produced 4.3 g of 7-chloro-2,2,3-trifluro-3-trifluoromethyl-2,3-dihydrobenzofuran as an oil. The nmr spectrum was consistent with the proposed structure.

Step C
7-Chloro-2,2,3-trifluoro-3-trifluoromethyl-2,3-dihydro-5-nitrobenzofuran A stirred mixture of 3.3 g (0.012 mole) 7-chloro-2,2,3-trifluoro-3-trifluoromethyl-2,3-dihydrobenzofuran, 10 ml of concentrated sulfuric acid and 15 ml of concentrated nitric acid was heated at 80° C. for approximately 18 hours. The mixture was cooled and poured into ice water. The aqueous mixture was extracted with three 100 ml portions of diethyl ether and the extracts were combined. After drying over anhydrous magnesium sulfate the extract was filtered. The filtrate was evaporated under reduced pressure leaving an oil which crystallized upon standing. Recrystallization from n-heptane yielded 1.65 g of 7-chloro-2,2,3-trifluoro-3-trifluoromethyl-2,3-dihydro-5-nitrobenzofuran (mp 46°-47° C.). The nmr and ir spectra were consistent with the proposed structure.

Analysis calc'd for $C_9H_2ClF_6NO_3$: C, 33.62; H, 0.62; Found: C, 33.00; H, 0.52.

Step D
5-Amino-7-chloro-2,2,3-trifluoro-3-trifluoromethyl-2,3-dihydrobenzofuran The hydrogenation of 1.6 g (0.0050 mole) 7-chloro-2,2,3-trifluoro-3-trifluoromethyl-2,3-dihydro-5-5nitrobenzofuran with a catalytic amount of platinum oxide (0.2 g) in 100 ml of methanol produced 1.4 g 5-amino-7-chloro-2,2,3-trifluoro-3-trifluoromethyl-2,3-dihydrobenzofuran.

The ir spectrum was consistent with the proposed structure.

Step E
N-[[(7-Chloro-2,2,3-trifluoro-3-trifluoromethyl-2,3-dihydrobenzofuran-5-yl)amino]carbonyl]-2,6-difluorobenzamide In a manner similar to Step D of Example 1, the reaction of 0.38 g (0.0025 mole) 2,6-difluorobenzamide, 0.33 g (0.0026 mole) oxalyl chloride, 0.7 g (0.0024 mole) 5-amino-7-chloro-2,2,3-trifluoro-3-trifluoromethyl-2,3-dihydrobenzofuran and 5 ml of methylene chloride in 75 ml of toluene produced 0.56 g of N-[[(7-chloro-2,2,3-trifluoro-3-trifluoromethyl-2,3-dihydrobenzo-5-yl)amino]carbonyl]-2,6-difluorobenzamide as a solid (mp 167.5°-170° C.), Compound 10 of Table 1.

The nmr and ir spectra were consistent with the proposed structure.

Analysis calc'd for $C_{17}H_7ClF_8N_2O_3$: C, 43.01; H, 1.48; Found: C, 44.26; H, 1.70.

In the normal use of the insecticidal benzoylureas of the present invention, the benzoylureas usually will not be employed free from admixture or dilution, but ordinarily will be used in a suitable formulated composition compatible with the method of application and comprising an insecticidally effective amount of benzoylurea. The benzoylureas of this invention, like most pesticidal agents, may be blended with the agriculturally acceptable surface-active agents and carriers normally employed for facilitating the dispersion of active ingredients, recognizing the accepted fact that the formulation and mode of application of an insecticide may affect the activity of the material. The present benzoylureas may be applied, for example, as sprays, dusts, or granules to the area where pest control is desired, the type of application varying of course with the pest and the environment. Thus, the benzoylureas of this invention may be formulated as granules of large particle size, as powdery dusts, as wettable powders, as emusifiable concentrates, as solutions, and the like.

Granules may comprise porous or nonporous particles, such as attapulgite clay or sand, for example, which serve as carriers for the benzoylureas. The granule particles are relatively large, a diameter of about 400-2500 microns typically. The particles are either impregnated with the benzoylurea from solution or coated with the benzoylurea, adhesive sometimes being employed. Granules generally contain 0.05-10%, preferably 0.5-5%, active ingredient as the insecticidally effective amount.

Dusts are admixtures of the benzoylureas with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as carriers for the insecticide. These finely divided solids have an average particle size of less than about 50 microns. A typical dust formulation useful for controlling insects contains 1 part of benzoylurea, such as N-[[(2,2,3,3-tetrafluoro-2,3-dihydrobenzofuran-6-yl)amino]carbonyl]2,6-difluorobenzamide, and 99 parts of talc.

The benzoylureas of the present invention may be made into liquid concentrates by dissolution or emulsification in suitable liquids and into solid concentrates by admixture with talc, clays, and other known solid carriers used in the pesticide art. The concentrates are compositions containing, as an insecticidally effective amount, about 5-50% benzoylurea, and 95-50% inert material, which includes surface-active dispersing, emulsifying, and wetting agents, but even higher concentrations of active ingredient may be employed experimentally. The concentrates are diluted with water or other liquids for practical application as sprays, or with additional solid carrier for use as dusts.

Typical carriers for solid concentrates (also called wettable powders) include fuller's earth, clays, silicas, and other highly absorbent, readily wetted inorganic diluents. A solid concentrate formulation useful for controlling insects contains 1.5 parts each of sodium lignosulfonate and sodium lauryl sulfate as wetting agents, 25 parts of N-[[(2,2,3,3-tetrafluoro-2,3-dihydrobenzofuran-5-yl) amino]carbonyl]-2,6-difluorobenzamide, and 72 parts of attapulgite clay.

Manufacturing concentrates are useful for shipping low melting products of this invention. Such concentrates are prepared by melting the low melting solid products together with one percent or more of a solvent to produce a concentrate which does not solidify on cooling to the freezing point of the pure product or below.

Useful liquid concentrates include the emulsifiable concentrates, which are homogeneous liquid or paste compositions readily dispersed in water or other liquid carriers. They may consist entirely of the benzoylurea with a liquid or solid emulsifying agent, or they may also contain a liquid carrier such as xylene, heavy aromatic naphthas, isophorone and other relatively non-volatile organic solvents. For application, these concentrates are dispersed in water or other liquid carriers and normally applied as sprays to areas to be treated.

Typical surface-active wetting, dispersing, and emulsifying agents used in pesticidal formulations include, for example, the alkyl and alkylaryl sulfonates and sulfates and their sodium salts; alkylamide sulfonates, including fatty methyl taurides; alkylaryl polyether alcohols, sulfates of higher alcohols, polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises about 1-15% by weight of the insecticidal composition.

Other useful formulations include simple solutions of the active ingredient in a solvent in which it is completely soluble at the desired concentrations, such as acetone or other organic solvents.

An insecticidally effective amount of benzoylurea in an insecticidal composition diluted for application is normally in the range of about 0.001% to about 8% by weight. Many variations of spraying and dusting compositions known in the art may be used by substituting the benzoylureas of this invention into compositions known or apparent in the art.

The insecticidal compositions of this invention may be formulated with other active ingredients, including other insecticides, nematicides, acaricides, fungicides, plant growth regulators, fertilizers, etc. In using the compositions to control insects, it is only necessary that an insecticidally effective amount of benzoylurea be applied to the locus where control is desired. Such locus may, e.g., be the insects themselves, plants upon which the insects feed, or the insect habitat. When the locus is soil, e.g., soil in which agricultural crops are or will be planted, the active compound may be applied to and optionally incorporated into the soil. For most applications, an insecticidally effective amount will be about 75 to 4000 g per hectare, preferably 150 g to 3000 g per hectare.

The insecticidal activity of the benzoylureas whose preparation is described above were formulated as 5% dust on a clay base using the following formulation:

|  | % w/w |
|---|---|
| Test Compound | 5.00 |
| Base | 95.00 |
| 96% Attaclay | |
| 2% highly purified sodium ligno-sulfonate (100%) | |
| 2% powdered sodium alkylnaphthalene sulfonate (75%) | |
| | 100.00 |

The formulations were prepared by mixing the test compound with the dry base.

Diet Incorporated Screen

The compounds of this invention were tested by incorporating the compounds into the diet of the test insects, second instar southern armyworm (*Spodoptera eridania*) and cabbage looper (*Trichoplusia ni*). The tests were conducted at rates of 200, 20, and 2 ppm, using ten larvae per replicate and two replicates per rate. Each test was read one day, three to five days, and six to eleven days after infestation to determine the number of dead after at least one molt.

The test media consisted of the formulation (dust) of the test compound mixed with the insect diet. The components of the test media and its method of preparation are:

| Composition of Insect Diet | |
|---|---|
| | Parts by Weight |
| Pinto beans | 12.90 |
| Wheat germ | 5.68 |
| Brewer's dried yeast | 3.64 |
| Ascorbic acid | 0.37 |
| Methyl paraben | 0.23 |
| Sorbic acid | 0.11 |
| Sodium benzoate | 0.00284 |
| Agar | 0.71 |
| Formalin (40%) | 0.23 |
| Water | 76.13 |

The agar was dissolved with heating in one-half the water and was brought to a boil. Simultaneously, all other ingredients except the formalin were placed in a blender with the remaining water and were reduced to a smooth, homogenous mixture. This mixture was added to the boiling agar. Immediately, the formalin was added with mixing.

Test media containing 200 ppm of the test compound were prepared by making a 'stock solution' from 1000 mg of the 5% dust formulation stirred well with 5 ml of distilled water in a vial. One milliliter of the 'stock solution' was added to 50 ml of warm, i.e. molten, insect diet in a plastic petri dish which was then mixed thoroughly. After cooling to room temperature, the gelled test media were infested with test larvae and covered.

Lower test rates were prepared by dilution of the 'stock solution' according to the following table:

| Desired Rate (ppm) | ml of 'stock solution' | ml of water |
|---|---|---|
| 20 | 1 | 9 |
| 2 | 1 ml of 20 ppm solution | 9 |

The results of diet incorporated testing are summarized in Table 2.

Foliar Evaluation

The compounds of this invention were tested in foliar evaluations against Mexican bean beetle (*Epilachna varivestis*), southern armyworm (*Spodoptera eridania*), and cabbage looper (*Trichoplusia ni*) according to the following procedure:

A test solution containing 500 ppm of the test compound was prepared by making a 'stock solution' from 250 mg of a 5% dust formulation, one drop of cotton seed oil, and one drop of octylphenoxypolyethoxyethanol in 25 ml of distilled water. Lower test rates were prepared by dilution of the 'stock solution' according to the following table:

| Desired Rate (ppm) | ml of 'stock solution' | ml of water* |
|---|---|---|
| 250 | 12.5 | 12.5 |
| 100 | 5.0 | 20.0 |
| 50 | 5.0 | 45.0 |
| 10 | 5.0 ml of 50 ppm | 20.0 |

*containing 10 drops each of cotton seed oil and octylphenoxypolyethoxyethanol per liter.

Other test rates were prepared by dilution of the stock solution with a suitable quantity of water.

The appropriate test solution of the test compound was sprayed on pinto bean plants to run-off, two replicates per test. Once the plants were dry, they were cut at the base of the stem. The stem of each plant was inserted into a hole made in the bottom of a wax coated paper cup, one plant per cup. Each plant was infested with ten first instar Mexican bean beetle, southern armyworm, or cabbage looper larvae to ensure that a molt would occur prior to reading the test. Cheese cloth was placed over the top of each cup and held in place by a lid with a 1" to 2.5" diameter hole. The cups containing the tests were placed in a rack which submerges the stem of each plant in a tray of distilled water. The tests were kept in a growth chamber at constant humidity (50%) and temperature (25° C.) for four days, at which time the tests were read. The results of these tests are summarized in Table 3.

TABLE 2

Diet Incorporated Screen % Kill

| Cmpd No. | Exposure Period (Days) | Insects[a] | | | | | |
|---|---|---|---|---|---|---|---|
| | | SAW (ppm) | | | CL (ppm) | | |
| | | 200 | 20 | 2 | 200 | 20 | 2 |
| 1 | 1 | 0 | 0 | 0 | 0 | 0 | 0 |
|   | 4 | 100 | 100 | 100 | 100 | 100 | 0 |
|   | 8 | 100 | 100 | 100 | 100 | 100 | 50 |
| 2 | 1 | 0 | 0 | 0 | 40 | 0 | 0 |
|   | 4 | 90 | 90 | 40 | 100 | 100 | 100 |
|   | 8 | 100 | 90 | 40 | 100 | 100 | 100 |
| 3 | 1 | 0 | 0 | 0 | 0 | 0 | 0 |
|   | 2 | 100 | 80 | 100 | 0 | 0 | 2 |
|   | 4 | 100 | 100 | 100 | 80 | 100 | 70 |
|   | 8 | 100 | 100 | 100 | 100 | 100 | 100 |
| 4 | 1 | 100 | 0 | 0 | 0 | 0 | 0 |
|   | 3 | 100 | 40 | 0 | 30 | 80 | 20 |
|   | 8 | 100 | 100 | 70 | 100 | 100 | 100 |
| 5 | 2 | 0 | 0 | 0 | 50 | 0 | 0 |
|   | 5 | 50 | 0 | 0 | 80 | 0 | 0 |
|   | 8 | 100 | 10 | 0 | 100 | 0 | 10 |
| 6 | 1 | 0 | 0 | 0 | 10 | 0 | 10 |
|   | 5 | 100 | 100 | 50 | 100 | 100 | 40 |
|   | 8 | 100 | 100 | 90 | 100 | 100 | 100 |
| 7 | 1 | 0 | 0 | 0 | 0 | 20 | 0 |
|   | 5 | 100 | 100 | 60 | 100 | 100 | 70 |
|   | 8 | 100 | 100 | 90 | 100 | 100 | 100 |
| 8[b] | 1 | | | | 0 | 0 | 0 |
|   | 5 | | | | 40 | 5 | 0 |
|   | 8 | | | | 95 | 5 | 0 |
| 9[b] | 1 | | | | 0 | 0 | 0 |
|   | 5 | | | | 100 | 0 | 0 |
|   | 8 | | | | 100 | 0 | 0 |
| 10[b] | 1 | | | | 0 | 0 | 0 |
|   | 5 | | | | 100 | 85 | 0 |

TABLE 1

2,2,3,3-TETRAFLUOROBENZOFURANYL BENZOYLUREAS

| Compd No. | A | B | R | W | Amino bond Position | M.P. (°C.) | Molecular Formula | Elemental Analysis | |
|---|---|---|---|---|---|---|---|---|---|
| | | | | | | | | C | H |
| 1 | F | F | H | O | 5 | 183–184.5 | $C_{16}H_8F_6N_2O_3$ | C 49.25<br>F 49.15 | 2.06<br>2.35 |
| 2 | F | F | H | O | 6 | 188–190 (dec) | $C_{16}H_8F_6N_2O_3$ | C 49.25<br>F 48.64 | 2.06<br>1.83 |
| 3 | F | F | 7-Cl | O | 5 | 219–220 (dec) | $C_{16}H_7ClF_6N_2O_3$ | C 45.25<br>F 45.48 | 1.66<br>1.63 |
| 4 | Cl | H | H | O | 6 | 174–176 (dec) | $C_{16}H_9F_4ClN_2O_3$ | C 49.44<br>F 49.25 | 2.33<br>2.31 |
| 5 | Cl | H | 7-Cl | O | 5 | 142–143 | $C_{16}H_8Cl_2F_4N_2O_3$ | C 45.42<br>F 47.62 | 1.90<br>2.20 |
| 6 | F | F | 4-Cl | O | 6 | 207–209 (dec) | $C_{16}H_7ClF_6N_2O_3$ | C 45.25<br>F 45.52 | 1.66<br>1.95 |
| 7 | Cl | H | 4-Cl | O | 6 | 172–174 (dec) | $C_{16}H_8Cl_2F_4N_2O_3$ | C 45.42<br>F 45.80 | 1.90<br>1.98 |
| 8 | F | F | 7-Cl | S | 5 | 208–209 | $C_{16}H_7ClF_6N_2O_2S$ | C 43.60<br>F 43.88 | 1.60<br>1.30 |
| 9 | H | Cl | 7-Cl | S | 5 | 140–142 | $C_{16}H_8Cl_2F_4N_2O_2S$ | C 43.75<br>F 43.41 | 1.83<br>1.77 |
| 10 | F | F | 7-Cl | O | 5 | 167.5–170 | $C_{17}H_7ClF_8N_2O_3$ | C 43.01<br>F 44.26 | 1.48<br>1.70 |
| 11 | H | Cl | 7-Cl | O | 5 | 145.5–147.5 | $C_{17}H_8Cl_2F_6N_2O_3$ | C 43.15<br>F 44.20 | 1.70<br>2.04 |

TABLE 2-continued

Diet Incorporated Screen % Kill

| Cmpd No. | Exposure Period (Days) | SAW (ppm) 200 | SAW (ppm) 20 | SAW (ppm) 2 | CL (ppm) 200 | CL (ppm) 20 | CL (ppm) 2 |
|---|---|---|---|---|---|---|---|
| 11[b] | 8 |  |  |  | 100 | 100 | 0 |
|  | 1 |  |  |  | 0 | 0 | 0 |
|  | 5 |  |  |  | 100 | 20 | 0 |
|  | 8 |  |  |  | 100 | 45 | 0 |

[a]Insects:
SAW—southern armyworm (*Spodoptera eridamia*)
CL—cabbage looper (*Trichoplusia ni*)
[b]Average of two tests

TABLE 3

FOLIAR EVALUATION OF TETRAFLUOROBENZOFURANYL BENZOYLUREAS % Kill

| Cmpd No. | Rate (ppm) | SAW | CL | MBB |
|---|---|---|---|---|
| 1 | 64 | 95 | 95 |  |
|  | 32 | 90 | 90 |  |
|  | 16 | 85 | 70 |  |
|  | 8 | 30 | 40 |  |
|  | 4 | 10 | 25 |  |
| 2 | 500 |  |  | 95[b] |
|  | 100 |  |  | 68[b] |
|  | 64 | 80 | 100 |  |
|  | 50 |  |  | 0 |
|  | 32 | 50 | 100 |  |
|  | 25 |  |  | 0 |
|  | 16 | 20 | 85 |  |
|  | 10 |  |  | 0 |
|  | 8 | 0 | 80 |  |
|  | 4 | 0 | 45 |  |
| 3 | 500 |  |  | 85 |
|  | 250 |  |  | 5 |
|  | 100 |  |  | 0 |
|  | 64 |  | 100 |  |
|  | 50 |  |  | 0 |
|  | 32 |  | 100 |  |
|  | 16 |  | 95 |  |
|  | 10 |  |  | 0 |
|  | 8 |  | 90 |  |
|  | 4 |  | 80 |  |
| 4 | 500 |  |  | 80 |
|  | 100 |  |  | 25 |
|  | 64 |  | 100 |  |
|  | 32 |  | 100 |  |
|  | 16 |  | 90 |  |
|  | 8 |  | 90 |  |
|  | 4 |  | 65 |  |
| 6 | 500 |  |  | 10 |
|  | 100 |  |  | 5 |
|  | 64 | 100 | 100 |  |
|  | 32 | 100 | 100 |  |
|  | 16 | 100 | 100 |  |

TABLE 3-continued

FOLIAR EVALUATION OF TETRAFLUOROBENZOFURANYL BENZOYLUREAS % Kill

| Cmpd No. | Rate (ppm) | SAW | CL | MBB |
|---|---|---|---|---|
|  | 8 | 100 | 100 |  |
|  | 4 | 80 | 90 |  |
| 7 | 500 |  |  | 80 |
|  | 100 |  |  | 50 |
|  | 64 | 100 | 100 |  |
|  | 32 | 100 | 100 |  |
|  | 16 | 95 | 100 |  |
|  | 8 | 90 | 100 |  |
|  | 4 | 90 | 100 |  |

[a]Insects:
SAW = southern armyworm (*Spodoptera eridania*)
CL = cabbage looper (*Trichoplusia ni*)
MBB = Mexican bean beetle (*Epilachna varivestis*)
[b]Average of two tests.

I claim:

1. A compound of the formula:

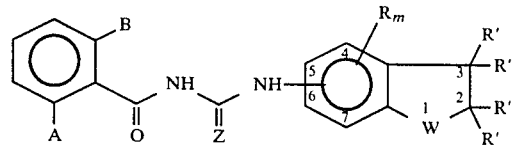

in which A and B are both hydrogen or halogen, or one of A and B is hydrogen, and the other of A and B is halogen; Z and W are independently O or S; the substituted benzofuranyl or benzothienyl group is attached at position 5 or 6; R is halogen; m is 0 to 3, R' is F or $CF_3$, with the proviso that only one of R' may be $CF_3$.

2. A compound of claim 1 in which A and B are selected from hydrogen, chlorine, or fluorine.

3. A compound of claim 2 in which R is chlorine and m is 0 or 1.

4. A compound of claim 3 in which A and B are both fluorine.

5. A compound of claim 3 in which one of A and B is chlorine and the other of A and B is hydrogen.

6. A compound of claim 3 in which m is 0, and W is oxygen.

7. A compound of claim 3 in which m is 1, and W is oxygen.

8. A compound of claim 3 in which one of R' is $CF_3$.

9. A compound of claim 3 in which m is 1 and W is sulfur.

10. An insecticidal composition comprising an insecticidally effective amount of a compound of claim 1 in admixture with a compatible agricultural carrier, diluent, or adjuvant.

11. A method for controlling insects by applying an insecticidally effective amount of a compound of claim 1 to the locus where control is desired.

* * * * *